United States Patent [19]
Geeslin et al.

[11] Patent Number: 5,711,671
[45] Date of Patent: Jan. 27, 1998

[54] AUTOMATED COGNITIVE REHABILITATION SYSTEM AND METHOD FOR TREATING BRAIN INJURED PATIENTS

[75] Inventors: Robert H. Geeslin, Sapulpa; Richard H. Bost, Catoosa, both of Okla.

[73] Assignee: The Board of Regents Of Oklahoma State University, Stillwater, Okla.

[21] Appl. No.: 755,708

[22] Filed: Nov. 25, 1996

Related U.S. Application Data

[63] Continuation of Ser. No. 272,418, Jul. 8, 1994, abandoned.
[51] Int. Cl.$^6$ .................................................. H04M 11/00
[52] U.S. Cl. ........................................... 434/236; 434/237
[58] Field of Search ........................... 434/219, 236–238, 434/262, 267, 270

[56] References Cited

U.S. PATENT DOCUMENTS

| | | |
|---|---|---|
| 4,836,670 | 6/1989 | Hutchinson . |
| 4,838,681 | 6/1989 | Pavlidis . |
| 4,839,822 | 6/1989 | Dormond et al. . |
| 5,002,491 | 3/1991 | Abrahamson et al. ............ 434/322 |
| 5,038,374 | 8/1991 | Kaufman et al. . |
| 5,047,930 | 9/1991 | Martens et al. . |
| 5,109,350 | 4/1992 | Henwood et al. . |
| 5,199,439 | 4/1993 | Zimmerman et al. . |
| 5,204,703 | 4/1993 | Hutchinson et al. . |
| 5,295,836 | 3/1994 | Ryu et al. ...................... 434/322 X |
| 5,377,258 | 12/1994 | Bro ................................... 379/93 |

Primary Examiner—Richard J. Apley
Assistant Examiner—Glenn E. Richman
Attorney, Agent, or Firm—Head, Johnson & Kachigian

[57] ABSTRACT

An automated cognitive rehabilitation system for treatment services for brain injured patients that enables one or more therapist each to remotely treat one or more patients, the system having a host computer including a data bank having stored therein an array of cognitive rehabilitation treatment procedures, and including memory for storing and evaluating responses, a plurality of therapist computer units each having a display and an input and each being in communication with the host computer so that the host computer data bank can be accessed for call up of selected cognitive rehabilitation procedures and a plurality of patient computer units each having a display and an input and each being in communication with the host computer so that the host computer data bank can be accessed to display selected cognitive rehabilitation procedures and receive and store responses thereto, which response are available to a therapist to enable the therapist to remotely select a cognitive rehabilitation treatment procedure that can then be independently accessed by a patient and the results reviewed by the therapist to enable the therapist to monitor progress of a patient and to prescribe additional procedures.

10 Claims, 4 Drawing Sheets

AUTOMATED COGNITIVE REHABILITATION SYSTEM AND METHOD FOR TREATING BRAIN INJURED PATIENTS

CROSS-REFERENCE TO RELATED APPLICATIONS

This application is a continuation of application Ser. No. 08/272,418 filed on Jul. 8, 1994 entitled "AN AUTOMATED COGNITIVE REHABILITATION SYSTEM AND METHOD FOR TREATING BRAIN INJURED PATIENTS", now abandoned.

REFERENCE TO MICROFICHE APPENDIX

This application is not referenced in any microfiche appendix.

BACKGROUND OF THE INVENTION

Disability from brain injury is common, costly, and ranks as one of this nation's major health problems. The National Center for Health Statistics estimated that the annual incidence of all head injuries (except those resulting in death) is 3,900 per 100,000 in the United States, and enhanced survivability resulting from improved medical treatment makes this a growing population. One study of the effects of traumatic brain injury showed that 42% of such patients experienced memory problems and 33% were unemployed three months after the injury. Another study further reported that head injury is the leading cause of disability in children and young adults in the United States. The effects of cerebrovascular accident are similarly debilitating. More than 500,000 people have strokes each year. While 10% have no disability, 40% have mild-to-moderate disability, 40% have severe disability, and 10% remain so disabled as to require institutionalization. It has been estimated that the economic cost of head injury approaches 25 billion dollars each year.

"Cognitive rehabilitation" is the term most commonly used to describe therapy efforts aimed at restoring or compensating for dysfunctional thinking abilities. These therapy efforts usually consist of a variety of activities. They typically include both individual and group therapy. The activities are tailored to meet the needs and capabilities of each individual patient.

Individual therapy is usually a part of a comprehensive cognitive rehabilitation regimen. This typically consists of repetitive face-to-face therapy sessions in which exercises designed to remediate dysfunctional cognitive skills or to build compensatory skills are practiced. These efforts require repetitive practice by the patient under the guidance of the therapist. Practice and repetition are essential to building or re-building skills. This principle is as true of training cognitive skills as it is for establishing any kind of competence. It is well established that therapy tasks should be administered repetitively. Therefore, when a cognitively impaired patient seeks treatment following discharge from an inpatient facility, maximizing repetitive practice is a necessary consideration in treatment planning. These practice efforts have traditionally been done in the therapist's office or clinic, where the therapist has a maximum opportunity to direct the patient's efforts.

Many therapists attempt to extend work done in face-to-face sessions by making home practice assignments. Such assignments have usually involved the same paper-and-pencil tools used during clinic/office sessions. However, use of these tools involves several limitations. First, this strategy typically requires teaching the patient's family how to administer the exercises. Administration of the exercises is usually time and effort intensive. The success of this strategy is limited by the time and energy family members have available to devote to such efforts. Second, the repetitive practice helpful to brain-injured persons can become very monotonous to non-injured family members. Third, success in such practice is limited by questionable reliability in administration and scoring due to limited training as well as emotional involvement of family members.

It has been pointed out that major problems with traumatically brain-injured patients after discharge from in-patient rehabilitation treatment include memory, judgement, cognition, and behavior problems. These remaining problems are frequently disabling, even after problems with walking, talking, and communicating have been resolved. They often prevent a patient from living independently, and often prevent a patient from successfully returning to work. Such patients frequently return home after completing in-patient rehabilitation needing rehabilitation only for these cognitive dysfunctions in order to return to independent living or to gainful employment.

Others have attempted to deal with these problems through the automation (or computerization) of such therapy activities. Automated exercises have been available for several years and have offered the advantages of increased reliability of administration and scoring and relief for family members from the tedious effort involved in repetitive practice. However, existing computerized systems have involved the purchase of expensive computer equipment and a fixed software package for each patient. Such purchases often involve a wide range of problems from the disposition of equipment and software after therapy to the limited capacity of published software packages to fully meet retraining needs of each individual patient.

The invention disclosed herein represents a major step in overcoming the limitations of known computerized systems. In contrast to the fixed software packages in traditional automated systems, the methods of this disclosure are dynamic. That is, this invention provides exercises that can be modified to compensate for many physical disabilities. The difficulty levels can also be adjusted to maximize the likelihood that patients will feel challenged and rewarded by their practice efforts.

The present invention provides exercises having the advantage of increasing reliability of exercise administration while decreasing the time and effort required of family members. The invention of this disclosure has the advantage of automatic compilation of the results of the patient's practice efforts, plus a distinct advantage in being able to report these results to the therapist via modem or facsimile at any time. Time and effort needed from family members using the services is usually limited to giving encouragement and emotional support to the patient as needed, rather than requiring the time and enduring the frustration often involved in setting up, operating, and maintaining a free-standing computer.

For patents issued on similar disclosures, reference may be had to the following United States patents:

| U.S. Pat. No. | TITLE |
| --- | --- |
| 4,836,670 | Eye Movement Detector |
| 4,839,822 | Computer System And Method For Suggesting Treatments For Physically Trauma |
| 4,838,681 | Method and Means For Detecting Dyslexia |
| 5,109,350 | Evaluation System |
| 5,038,374 | Data Transmission and Storage |
| 5,047,930 | Method and System For Analysis Of Long Term Physiological Polygraphic Recordings |
| 5,199,439 | Medical Statistical Analyzing Method |
| 5,204,703 | Eye Movement and Pupil Diameter Apparatus and Method |

BRIEF SUMMARY OF THE INVENTION

This invention provides an automated cognitive rehabilitation system that makes a library of computerized cognitive rehabilitation exercises available to the patient and his/her therapist via computer modem. The system facilitates patient registration, prescription of exercises and their parameters (e.g. difficulty level, speed of stimulus presentation etc.), and feedback of practice results to the therapist. The therapist will typically relay these results to the patient's insurers. The electronic flow of these exercises and this information can be summarized as follows:

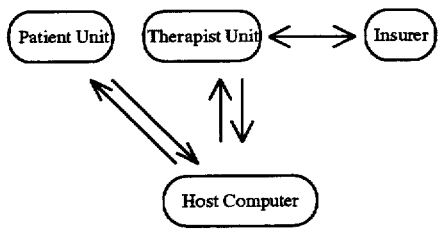

The therapist registers the patient and prescribes the appropriate exercise(s) via modem with the host computer. Once registered, the patient can call up the first prescribed exercise simply by turning on the patient unit in his/her home. The patient's unit automatically establishes contact via modem with the host computer. The host computer then automatically downloads the exercise into the patient's unit. After the patient has finished practicing an exercise, the patient's unit automatically downloads the scores produced by the practice to the host computer. Each interchange between a patient's unit and the host computer typically takes from ten to fifty seconds; each practice session typically involves two computer-generated phone calls which last only a few seconds each. Thus, the patient can practice a session as often as desired.

The automated cognitive rehabilitation system of this invention, from the technological point of view, centers on the host computer which serves as a "lending library" of cognitive rehabilitation exercises. Any number of patients at any distance from the host computer can be brought on-line, where they will receive their treatment activities, as prescribed by their therapist. Or, if therapists wish, they may use the host computer in an office, clinic or hospital as an on-site rehabilitation device that allows direct observation. The host computer will store the data resulting from a patient's use under either circumstance, resulting in a production of a large data base, over time, which provides opportunity for research. Additionally, the host computer provides an administrative or office supervision functions for therapists, as it can contain programs that allow on-line registration of patients, on-line prescriptions to be entered and updated at any time, the assessing of clinical progress, and it provides instant data for administrative report development and for comparative reports to third party payers.

The "lending library" of cognitive rehabilitation exercises is organized according to commonly recognized cognitive domains.

In summary, the automated cognitive rehabilitation system of this disclosure represents an advance in the extension of therapist-directed cognitive rehabilitation efforts into patients' homes. This extension increases the effectiveness of face-to-face therapy by increasing available practice time. At the same time, utilization of the automated cognitive rehabilitation exercises prevents the use of more costly services in two ways. First, the need for costly individual face-to-face sessions is decreased; in-home practice substitutes for some face-to-face therapy. Second, the use of this system makes costly purchase of computer hardware and software unnecessary. The patient may simply lease the necessary hardware, that is, a personal computer and modem since the prescribed exercises with the specified parameters for each practice session by the therapist is downloaded from the host computer "lending library" of cognitive rehabilitation software.

A better understanding of the invention will be obtained from the following detailed description and claims taken in conjunction with the attached drawings.

DESCRIPTION OF THE PREFERRED EMBODIMENTS

Figure 1:
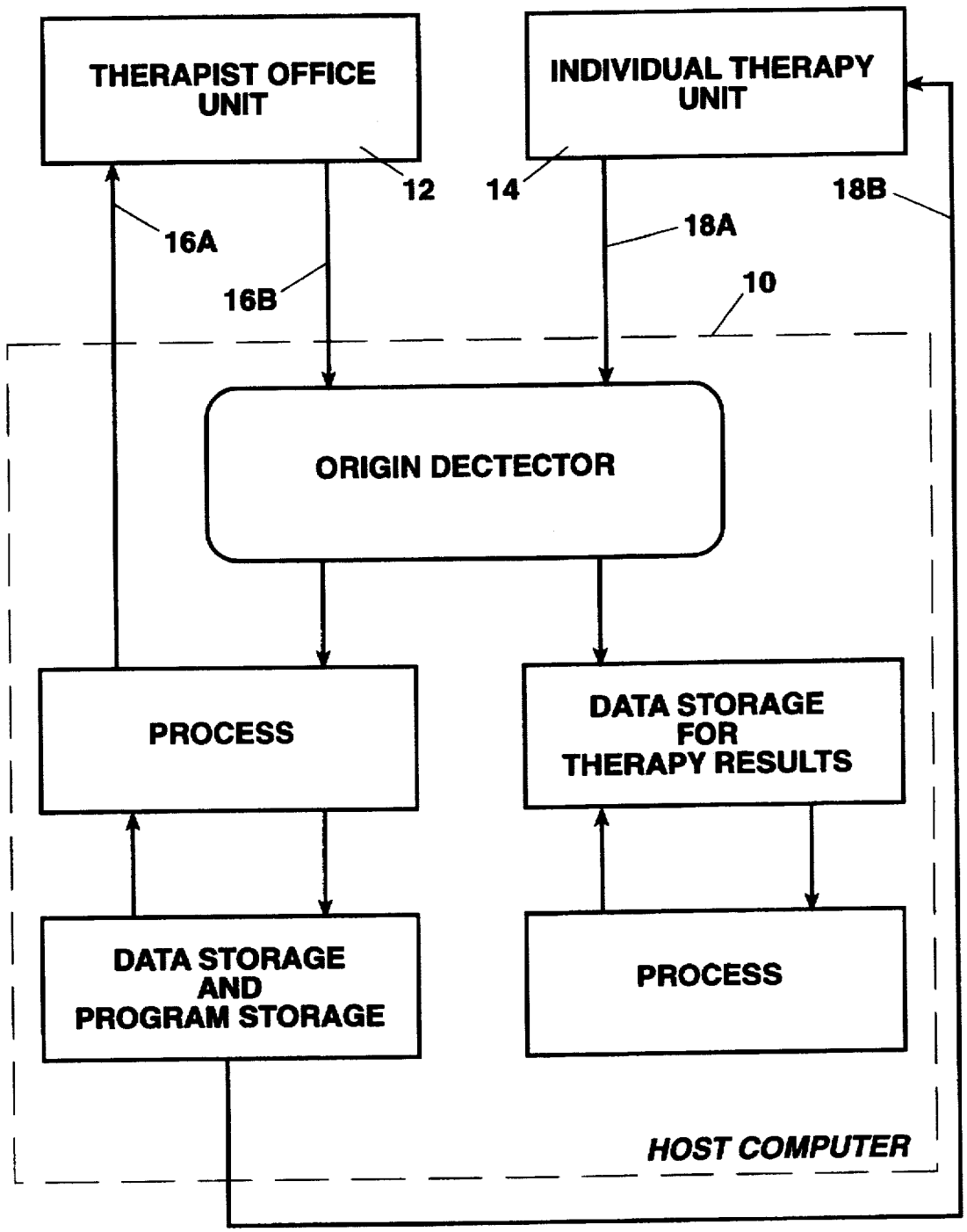
FIG. 1 is a block diagram showing the basic units making up the system of this invention by which the method of providing cognitive rehabilitation treatment services for brain injured patients is provided.

Referring to the drawings and first to FIG. 1, the basic elements making up the system for practicing the method of automated cognitive rehabilitation treatment for brain injured patients is shown. The basic components include a host computer 10, a therapist office unit 12 and an individual therapy unit 14 which also may be referred to as a "patient computer unit". These separate units 10, 12 and 14 can be remotely located from each other and can be in different cities, different states or even in different countries. Therapist office unit 12 connects with host computer 10 by a communication means indicated by information paths 16A and 16B which can, by example, be provided by a single telephone line in which a modem is used to connect the therapist office unit 12 with host computer 10.

In like manner, the individual therapy unit 14 is connected with host computer 10 by a second communication channel indicated by information paths 18A and 18B which may also be provided by a telephone line using a modem.

The basic information paths that take place in the host computer are indicated in FIG. 1. These information paths are indicative of the flow of information and not of actual processing equipment. For information as to the make-up of a host computer, reference should now be had to FIG. 2. However, before referring to FIG. 2 it should be pointed out that in the basic system for practicing the method of automated cognitive rehabilitation as set forth in FIG. 1, it is not necessary that direct communication be provided between the therapist office unit and the individual therapy unit except by way of host computer 10.

Figure 2:
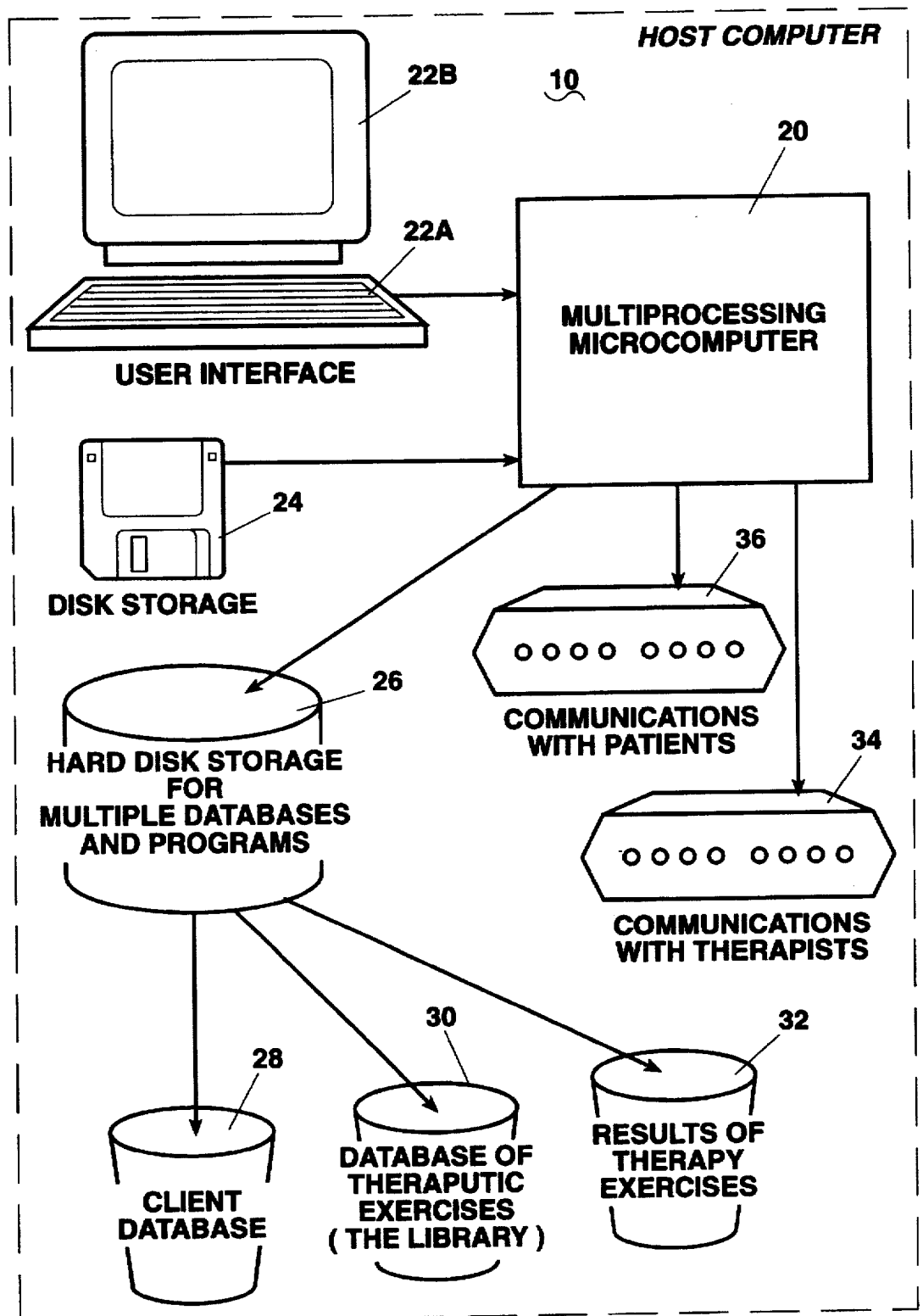
FIG. 2 diagrammatically illustrates the basic components making up the host computer as utilized in the system illustrated in FIG. 1.

Referring now to FIG. 2, the basic structural elements making up the host computer are illustrated to further explain the system employed and practiced in the method of this invention. The host computer essentially includes a microcomputer 20 having a connection with a user interface made up of a keyboard 22A and a video display 22B. The user interface 22A and 22B is employed to access memory of storage within host computer 10 so as to encode into the host computer an array of cognitive rehabilitation treatment procedures. These treatment procedures are commonly employed in neuropsychological evaluation and treatment of brain injured persons and derived within psychophysiciological-neuropsychological laboratories such as at the Oklahoma State University Clinic of the Oklahoma State University College of Osteopathic Medicine in Tulsa, Okla. This invention and the disclosure thereof is not related to a specific neuropsychological treatment procedure since the host of such procedures exist and are continuously being developed and upgraded. This invention consists essentially of challenging the mental facilities of a brain injured patient, such as proposing a question to a brain injured patient with multiple choice questions or multiple choice decisions in a sequence wherein the selection of an answer to a question, or a decision in response to a described situation, leads to progressively other questions or decision requirements to retrain the mental processes of a patient whose brain has been injured by some trauma. A whole array or library of such treatment procedures, each provided with an identification access code, can be placed into the data bank of the host computer utilizing the user interfaces exemplified by the keyboard 22A and video display 22B. The input may arise from a disk storage 24 that is generated elsewhere and imputed into the host computer library by access to the multiprocessing microcomputer 20.

The library within the host computer can be stored on hard disk 26 which can, by example, include memory storage indicating client database 28, a database or library of therapeutic exercises 30 as well as the results of therapeutic exercises given to a plurality of patients being treated, the storage of the results being indicated by 32.

As indicated in FIG. 1, host computer 10 must have communication with a therapist as indicated by 34. This may be in the form of a modem or other means of providing communication which can be conveniently achieved by the use of a telephone communication system. In like manner, communication must be provided between the host computer and microprocessing microcomputer by means of a communication system indicated by the numeral 36 which can also be achieved such as by a modem to couple the host computer through a telephone system to a therapist office.

Figure 3:
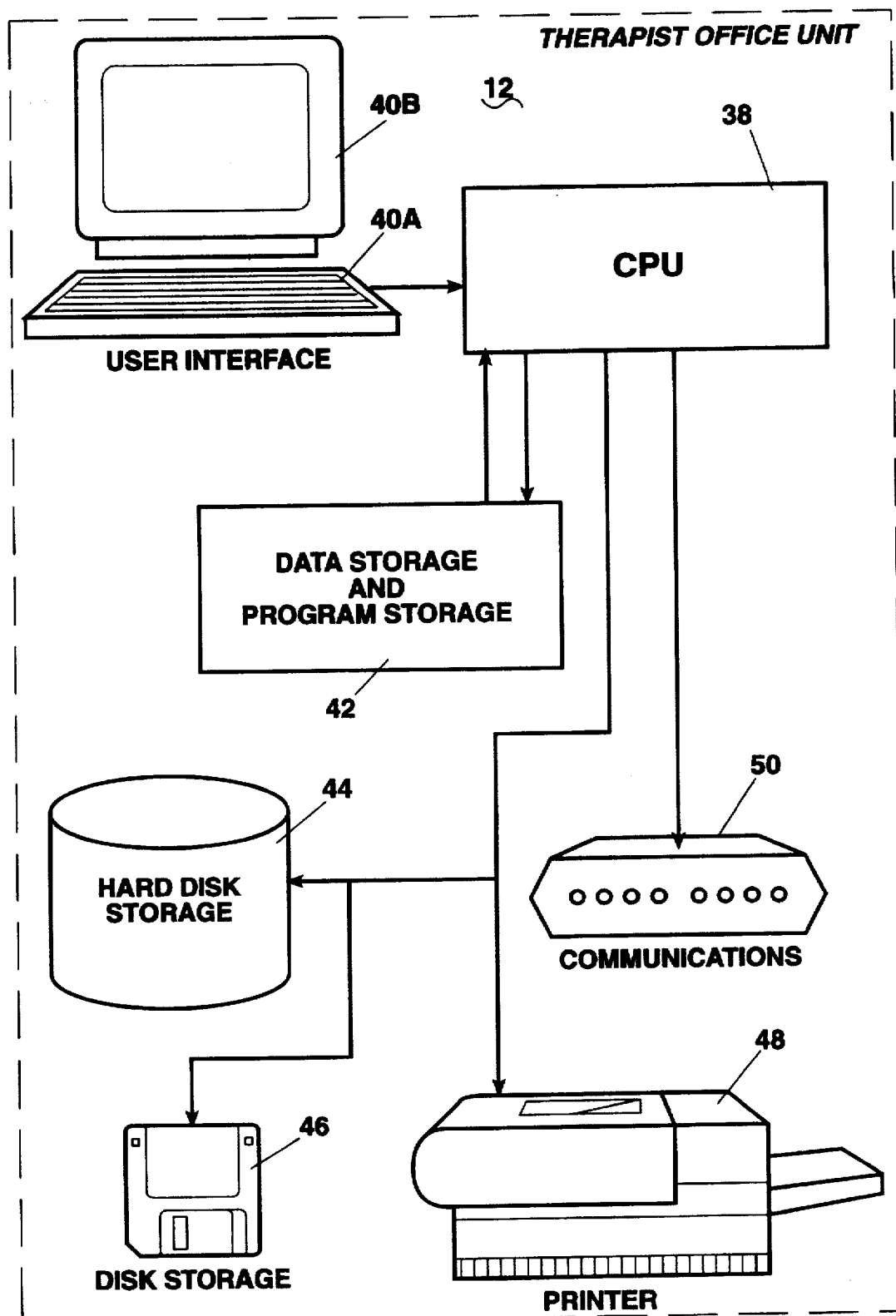
FIG. 3 diagrammatically illustrates the components making up the therapist office unit as illustrated in FIG. 1.

FIG. 3 illustrates the basic components making up a therapist office unit 12 which can be essentially, a personal computer, that is, a system having the basic elements of a personal computer. These elements include a central processing unit 38 (CPU), a user interface including a keyboard 40A and video display 40B, and provision for data storage and program storage 42. Memory is provided by hard disk 44 or by removable floppy disk 46. The elements 38, 40A, 40B, 42, 44 and 46 are all typical elements of a personal computer. An accessory element that is frequently used with personal computers and that is very useful to a therapist is a printer 48 by which information from the CPU can be permanently visibly displayed for use by the therapist.

As discussed with reference to FIG. 1, communication must be provided from the therapist office unit 12 to the host computer as indicated by the numeral 50 as seen in FIG. 3. The communication can be in the form of a modem connecting the therapist office unit 12, such as a personal computer, by a telephone system to the host computer.

Figure 4:
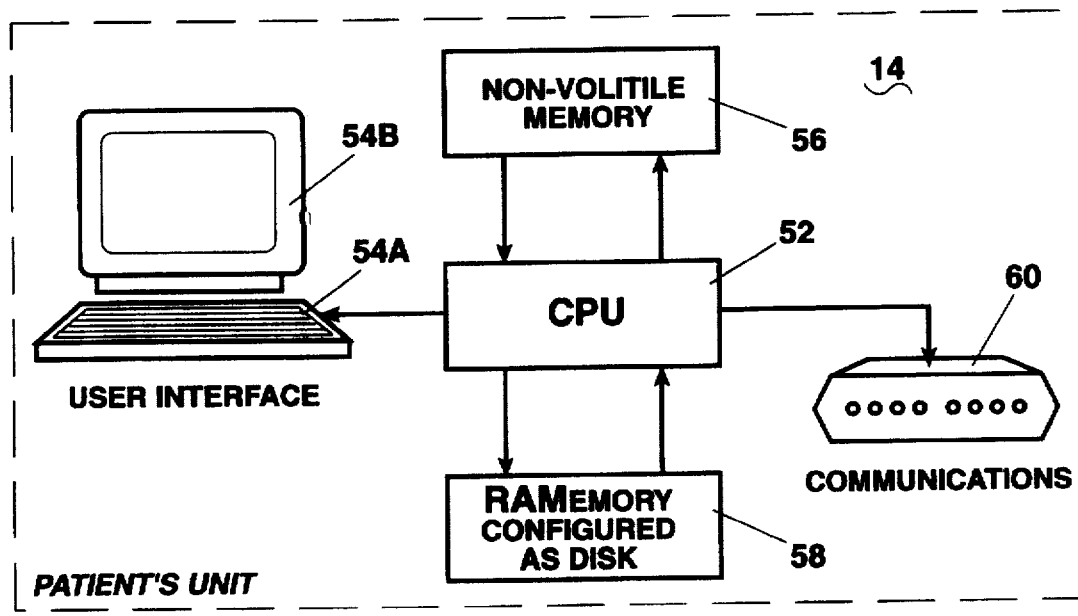
FIG. 4 is a block diagram illustrating the components making up the individual therapy unit as illustrated in FIG. 1.

FIG. 4 illustrates the basic components making up the individual therapy unit, which may also be referred to as a "patient computer unit", which can be typically a personal computer. The basic elements of the individual therapy unit are the same as those of a personal computer, that is, a central processing unit 52, a user interface made up of a keyboard 54A, a video display 54B, non-volitile memory 56, such as provided by disk 58 and random access memory (RAM). As described with reference to FIG. 1, communication must also be provided between the individual therapy unit 14 and the host computer which is illustrated by the numeral 60. It can also be in the form of a modem connected with a telephone line.

Instead of the use of modem/telephone line communication systems, obviously the communication can be supplied by more exotic systems such as the use of satellite communication, optical fiber communication, cable television channel communication and so forth. The suggested use of telephone lines and modems arises because of the universal access of such communication means, and the description herein suggesting the use of a telephone line and modem as a means of interconnecting the host computer with a therapist office unit 12 or the host computer with the individual therapy unit 14 is by way of example only and not by way of limitation.

The operation of the host computer 10, therapist office unit 12 and individual therapy unit 14 each require individual internally provided software for originating, treating, processing, storing, retrieving, displaying and, otherwise, making use of information. The basic processes involved as supplied by applicable software for a reprogrammable, single function therapy unit are as follows:

TABLE I
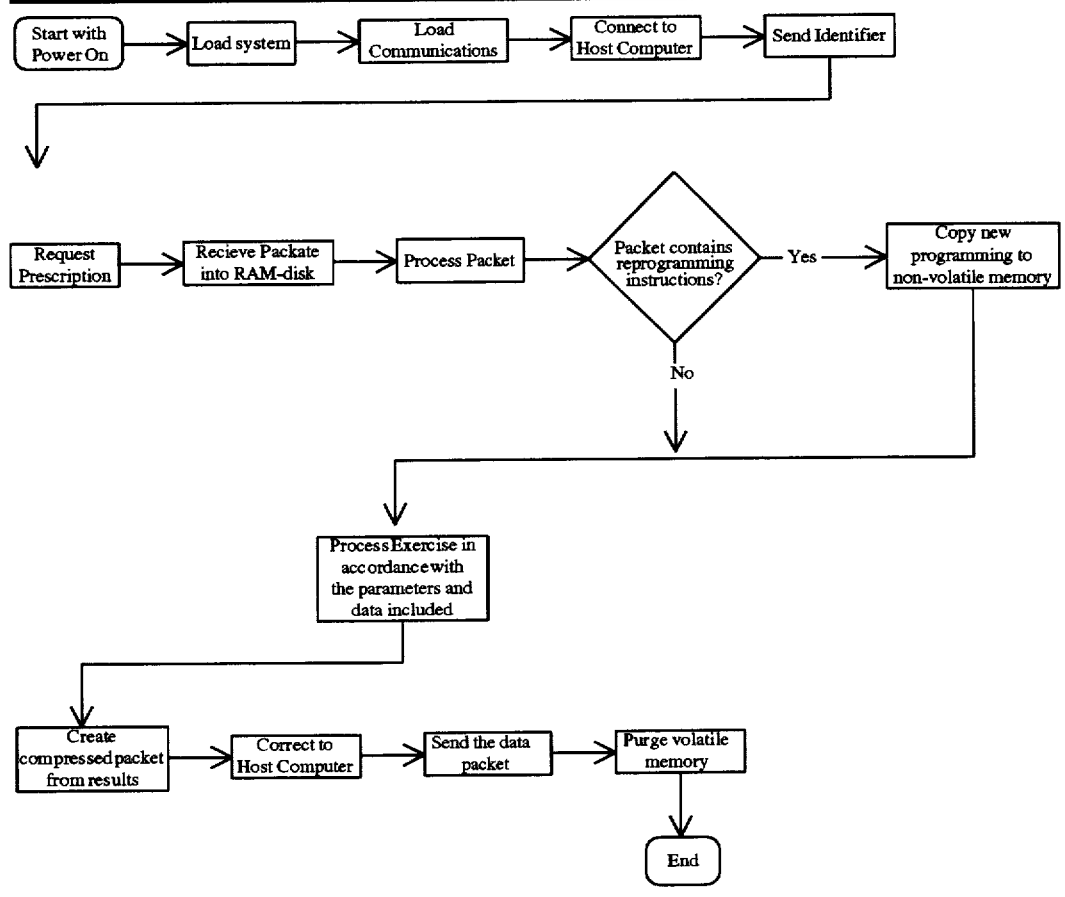
The flow of information within the host computer 40 achieved by proper software is as follows:

TABLE II
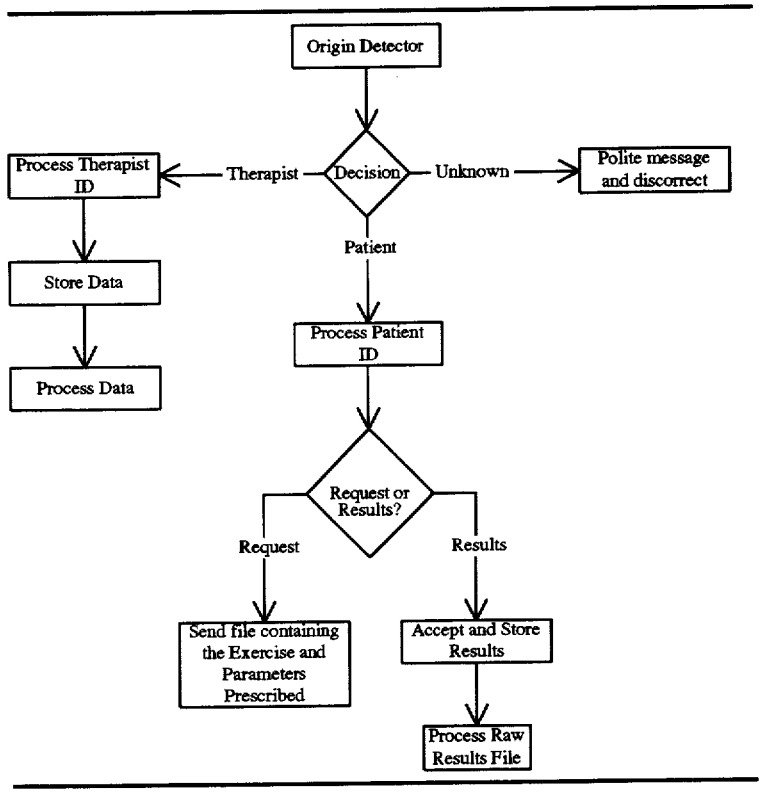
The origin detector system as illustrated above can be further broken down into the following steps that are incorporated in most computer software:

TABLE III

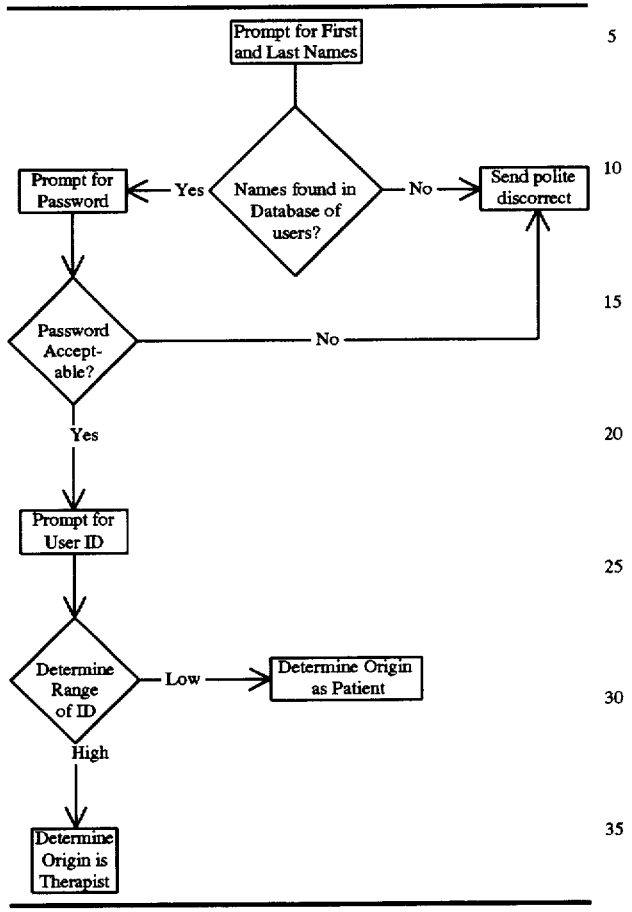

In FIG. 1, an important function of the host computer is labeled by the two blocks each identified by "Process". An example of the process contemplated for feeding information into and receiving it from the data storage and program storage is illustrated in Table II.

In the above, the block entitled "Process Data" can be further broken down into the following step:

TABLE IV
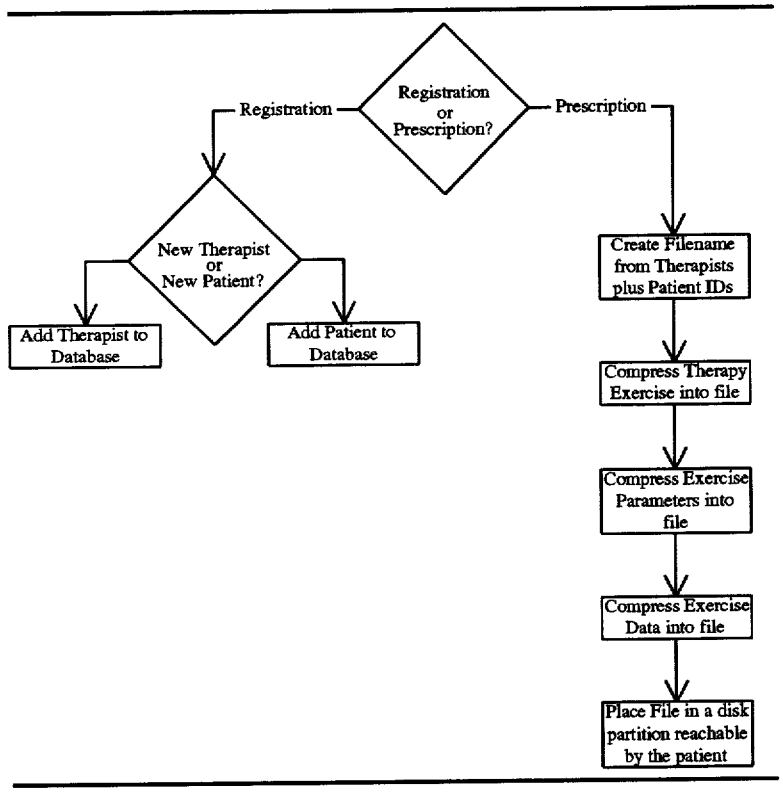
One of the final steps in the above flow chart as seen on Page 17 is entitled "Process Raw Results File". This can be further broken down in the sequence of steps as follows:
TABLE V
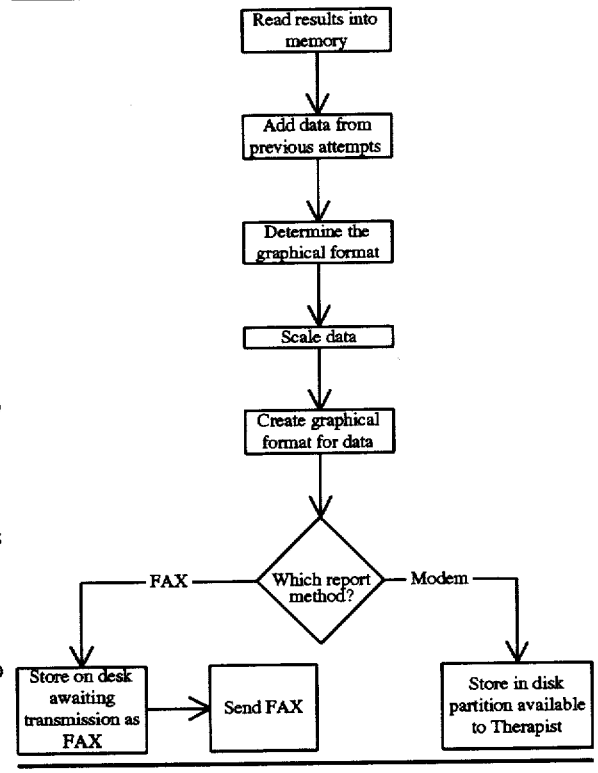
The flow charts above representing processing steps achieved by proper software are intended to illustrate the methods of imputing and using an array of cognitive rehabilitation treatment procedures which can be selectively accessed by a therapist and made available by action of the therapist to a patient when the patient, by use of an individual therapy unit on his own time and own volition, elects to access the host computer.

Figure 5:
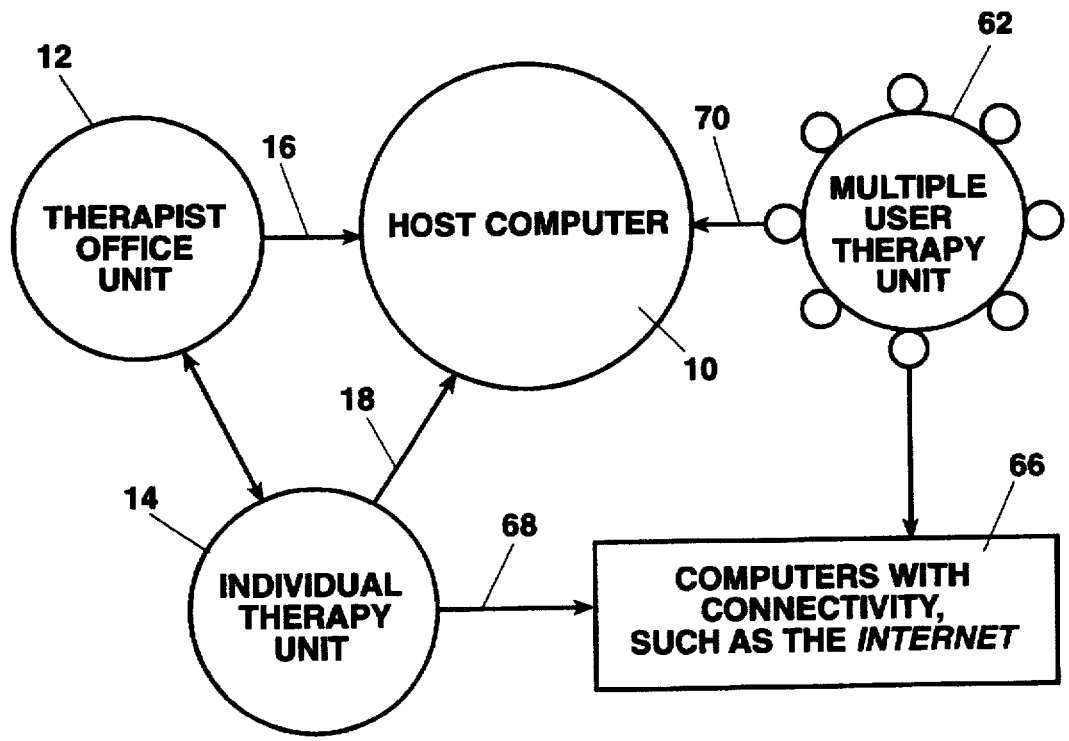
FIG. 5 illustrates an alternate embodiment of the invention employing a multiple user therapy unit providing means whereby interaction can be achieved between patients undergoing therapy utilizing the automated cognitive rehabilitation system and methods of this invention.

Many therapists believe that interaction with other people is a primary consideration to fully recover spontaneity and complex reasoning by a patient. FIG. 5 illustrates an expansion of the basic system of FIG. 1 that adds to this basic system multiple user therapy unit 62 together with a means for interconnecting the computers with a network such as "Internet" indicated by the numeral 66. Thus, an individual utilizing an individual therapy unit 14 can, by communication means 68, connect with a network 66 which in turn allows the patient to establish communication with other patients through the multiple user therapy unit 62. In turn, by a communication system 70 which can be in the form of a telephone line, the multiple user therapy unit can be connected to the host computer or the multiple user therapy unit may be physically located adjacent to the host computer or, in fact, structurally incorporated within it. The system of FIG. 5, as indicated above, allows a plurality of patients to interact with each other as a part of the rehabilitation process.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An automated rehabilitation system for treating a plurality of remotely located patients by a plurality of remotely located therapists comprising:

a host computer including a data bank having stored therein an array of treatment procedures, and including memory for storing response data;

a separate therapist computer unit for use by each of said remotely located therapists, each computer unit having a display and an input;

a plurality of remotely located patient computer units, one for each patient, each having a display and an input;

first communication means providing communication between each said therapist's computer unit and said host computer including means whereby said host computer data bank can be accessed independently and simultaneously by each said therapist for call up of said response data separately from each said patient of each said therapist for evaluation of the response data of each said patient including means whereby each said therapist may separately and simultaneously select rehabilitation procedures for each said patient; and second communication means providing communication between each of said patient computer units and said host computer whereby said host computer data bank can be accessed by each said patient computer units to display a rehabilitation procedure specifically selected for each patient by a therapist, said host computer having means to receive and store response data arising therefrom, which response data are available to a therapist by said first communication means whereby each said therapist can remotely select a rehabilitation treatment procedure for each of said therapist's patients that may time independently be accessed individually by said patients and the results thereof stored in said host computer to be time independently accessed by said therapists to enable each said therapist to monitor progress of a plurality of separate, remotely located patients and to prescribe additional, future treatment procedures.

2. An automated rehabilitation system according to claim 1 wherein said first communication means comprises a telephone circuit accessed by a modem interconnection with each said therapist computer unit.

3. An automated rehabilitation system according to claim 1 wherein said second communication means comprises a telephone circuit accessed by a modem interconnection with each said patient computer unit.

4. An automated rehabilitation system according to claim 1 wherein said host computer includes means to store and summate responses from a plurality of said patient computer units for use in conducting research of rehabilitation procedures.

5. An automated rehabilitation system according to claim 1 including:

a network computer; and means to interconnect a plurality of said patient computer units through said network computer to provide interaction between patients remotely located from each other.

6. A method of applying cognitive rehabilitation therapy to a plurality of different remotely located brain injured patients by a plurality of different remotely located therapists, each therapist having an individual set of remotely located patients, comprising the steps of:

(1) providing a bank of data in a host computer having stored therein an array of separately selectable cognitive rehabilitation treatment procedures and memory for storing data reflecting patient responses;

(2) prescribing individually by each of a plurality of remotely located therapists, each having a therapist computer unit cognitive rehabilitation treatment procedures individually to a plurality of different, remotely located patients;

(3) communicating said instruction from step (2) to said host computer;

(4) communicating prescribed cognitive rehabilitation treatment procedures from step (2) from said host computer selectively to each of said plurality of remotely located patient computer units, each patient computer unit being located for convenient access by a said patient, each communication being in response to a patient initiated contact from a said patient computer unit to said host computer;

(5) recording in memory in said host computer data generated by patients responses to said cognitive rehabilitation treatment procedure of step (4) for each of said patients, which responses are indicative of the progress of cognitive rehabilitation of each patient; and (6) accessing individually said patient responses stored in said host computer by each of said therapists to enable each said therapist to evaluate the progress of each of said therapist's patients and to thereby enable each said therapist to prescribe further instructions for further cognitive rehabilitation treatment procedures for each of said therapist's patients.

7. A method of applying cognitive rehabilitation therapy according to claim 6 wherein said step of communicating instructions from each of said therapist to said host computer is by use of a separate telephone circuit accessed by a modem for each said therapist.

8. A method of applying cognitive rehabilitation therapy according to claim 6 wherein said step of communicating instructions from said host computer to each of said patients is by use of separate telephone circuits accessed by a modem for each of said patients.

9. A method of applying cognitive rehabilitation therapy according to claim 6 including the step of storing and summating responses from said plurality of patients and using the summated responses for conducting research of cognitive rehabilitation procedures.

10. A method of applying cognitive rehabilitation therapy according to claim 6 including the step of interconnecting a plurality of patient computer units through a network computer to produce interaction between patients remotely located from each other.

* * * * *

UNITED STATES PATENT AND TRADEMARK OFFICE
CERTIFICATE OF CORRECTION

PATENT NO. : 5,711,671

DATED : January 28, 1997

INVENTOR(S) : Robert H. Geeslin et al.

It is certified that error appears in the above-identified patent and that said Letters Patent is hereby corrected as shown below:

Col. 7, TABLE I, in the second box in the next-to-last line of boxes of the flow diagram, delete "Correct to Host Computer" and substitute --Connect to Host Computer-- therefor.

Signed and Sealed this

Fourteenth Day of April, 1998

Attest:

BRUCE LEHMAN

Attesting Officer

Commissioner of Patents and Trademarks